(12) United States Patent
Goto et al.

(10) Patent No.: US 6,262,275 B1
(45) Date of Patent: Jul. 17, 2001

(54) HERBICIDAL 1-SUBSTITUTED METHYL-TETRAZOLINONES

(75) Inventors: Toshio Goto; Yoshinori Kitagawa, both of Tochigi; Seishi Ito, Oyama; Katsuhiko Shibuya, Tochigi; Chieko Ueno, Tochigi; Yoshiko Kyo, Tochigi, all of (JP)

(73) Assignee: Nihon Bayer Agrochem K.K., Ibaraki (JP)

( * ) Notice: Subject to any disclaimer, the term of this patent is extended or adjusted under 35 U.S.C. 154(b) by 0 days.

(21) Appl. No.: 09/368,475

(22) Filed: Aug. 4, 1999

Related U.S. Application Data

(62) Division of application No. 08/890,432, filed on Jul. 9, 1997, now Pat. No. 6,017,853.

(30) Foreign Application Priority Data

Jul. 16, 1996 (JP) .................................................. 8-204179

(51) Int. Cl.[7] .................................................. C07D 413/06
(52) U.S. Cl. .................................................. 548/247
(58) Field of Search .............................................. 548/247

(56) References Cited

U.S. PATENT DOCUMENTS

| | | |
|---|---|---|
| 4,618,365 | 10/1986 | Covey et al. . |
| 4,826,529 | 5/1989 | Covey et al. . |
| 4,830,661 | 5/1989 | Covey et al. . |
| 4,956,469 | 9/1990 | Covey et al. . |
| 5,003,075 | 3/1991 | Covey et al. . |
| 5,019,152 | 5/1991 | Covey et al. . |
| 5,136,868 | 8/1992 | Theodoridis . |
| 5,342,954 | 8/1994 | Goto et al. . |
| 5,344,814 | 9/1994 | Goto et al. . |
| 5,347,009 | 9/1994 | Goto et al. . |
| 5,347,010 | 9/1994 | Goto et al. . |
| 5,362,704 | 11/1994 | Goto et al. . |
| 5,502,204 | 3/1996 | Yanagi et al. . |
| 5,530,135 | 6/1996 | Yanagi et al. . |
| 5,541,336 | 7/1996 | Goto et al. . |
| 5,589,439 | 12/1996 | Goto et al. . |
| 5,767,286 | 6/1998 | Yanagi et al. . |

FOREIGN PATENT DOCUMENTS

| | | |
|---|---|---|
| 0 692 482 A2 | 1/1996 | (EP) . |
| 0 695 748 A1 | 2/1996 | (EP) . |
| 0 708 097 A1 | 4/1996 | (EP) . |
| 0 711 761 A1 | 5/1996 | (EP) . |
| 0 712 850 A1 | 5/1996 | (EP) . |
| 0 728 750 A1 | 8/1996 | (EP) . |
| 0 732 326 A1 | 9/1996 | (EP) . |
| 0 733 624 A1 | 9/1996 | (EP) . |
| 0 733 625 A1 | 9/1996 | (EP) . |
| 0 771 797 A1 | 5/1997 | (EP) . |

OTHER PUBLICATIONS

A. Bell et al., "A QSAR Study of Substituted Tetrazolinone Herbicides", 1987 British Crop Protection Conference—Weeds, pp. 249–255.

G. Theodoridis et al., "Synthesis and Structure—Activity Relationships of 1–Aryl–4–. . . Herbicides", Pestic.Sci. 1990, 30, pp. 259–274.

*Primary Examiner*—Patricia L. Morris
(74) *Attorney, Agent, or Firm*—Norris McLaughlin & Marcus

(57) ABSTRACT

Novel 1-substituted methyltetrazolinones of the formula (I)

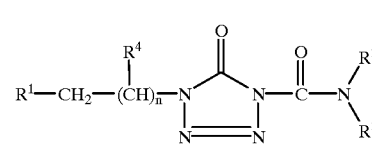

wherein $R^1$ represents a 5-membered heterocyclic radical which has 1 to 3 heteroatoms selected arbitrarily from the group consisting of N, O and S and which is optionally substituted by halogen and/or $C_{1-4}$ alkyl, or represents oxiran-2-yl, optionally chloro-substituted pyridyl or $C_{1-4}$ alkyl-S(O)$_m$— wherein m represents 0, 1 or 2, or represents a $C_{3-6}$ alicyclic hydrocarbon radical; $R^2$ and $R^3$ represent, independently of one another, $C_{1-6}$ alkyl, $C_{3-7}$ cycloalkyl or optionally substituted phenyl, or $R^2$ and $R^3$ may form, together with the N-atom to which they are bonded, an optionally substituted ring; $R^4$ represents a hydrogen atom or methyl; and n represents 0 or 1; as well as for their preparation processes and novel intermediates in their production. The inventive compounds of formula (I) are used as herbicides.

1 Claim, No Drawings

HERBICIDAL 1-SUBSTITUTED METHYL-TETRAZOLINONES

This application is a divisional application of U.S. Ser. No. 08/890,432, filed on Jul. 9, 1997, now U.S. Pat. No. 6,017,853.

The present invention relates to novel 1-substituted methyltetrazolinones, processes for their preparation and their use as herbicides as well as novel intermediates therefore.

It has already been known that certain tetrazolinones possess herbicidal activity (see EP-A-146,279).

These previously known compounds, however, have not been fully satisfactory in respect of their herbicidal effect and phytotoxicity on crop plants.

Now it has been discovered that novel 1-substituted methyltetrazolinones of the formula (I)

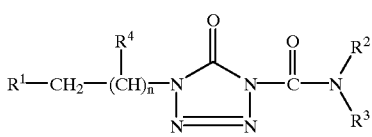
(I)

wherein
R$^1$ represents a 5-membered heterocyclic radical which has 1 to 3 heteroatoms selected arbitrarily from the group consisting of N, O and S and which is optionally substituted by halogen and/or C$_{1-4}$ alkyl, or represents oxiran-2-yl, optionally chloro-substituted pyridyl or C$_{1-4}$ alkyl-S(O)$_m$— wherein m represents 0, 1 or 2, or represents a C$_{3-6}$ alicyclic hydrocarbon radical, R$^2$ and R$^3$ represent, independently of one another, C$_{1-4}$ alkyl, C$_{3-7}$ cycloalkyl or optionally substituted phenyl, or R$^2$ and R$^3$ may form, together with the N-atom to which they are bonded, an optionally substituted ring, R$^4$ represents a hydrogen atom or methyl, and n represents 0 or 1 have surprisingly superior activity.

The compounds of the formula (I) according to the invention can be produced, for instance, by the following process in which
process (a):
compounds of the formula (II)

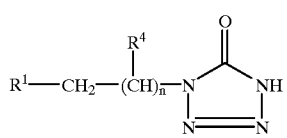
(II)

wherein
R$^1$, R$^4$ and n are defined as above,
are reacted with compounds of the formula (III)

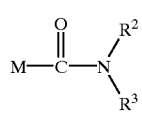
(III)

wherein
R$^2$ and R$^3$ are defined as above, and

M represents a leaving radical such as chloro or bromo, in the presence of an inert solvent, and if appropriate in the presence of a base.

The compounds of the formula (I) according to the invention have strong herbicidal activity and they exhibit very superior herbicidal action as well as better compatibility with crop plants in comparison to the previously known compounds which are similar to those of the formula (I) described in the above EP-A-146,279.

Therefore, the compounds according to the invention are extremely useful as herbicides.

In this specification, the term "5-membered heterocyclic radical" includes a monovalent radial consisting of a saturated, unsaturated or partially unsaturated 5-membered heterocyclic ring which has 1 to 3 identical or different heteroatoms selected from the group consisting of N, O and S. Preferably, it represents a monovalent radical consisting of an unsaturated 5-membered heterocyclic ring having one or two N atom(s) and one O atom or one S atom; two N atoms; or one S atom or O atom. Specific examples thereof include, for example, isoxazolyl, pyrazolyl, 1,2,5-oxadiazolyl, 1,3,4-oxadiazolyl, thiazolyl, isothiazolyl, thienyl, furyl, imidazolyl, 1,2,3-oxadiazolyl, 1,2,4-oxadiazolyl and 1,3,4-thiadiazolyl.

The term "halogen" includes fluorine, chlorine, bromine and iodine, preferably being fluorine, chlorine or bromine.

The term "C$_{3-6}$ alicyclic hydrocarbon radical" refers to a saturated or partially unsaturated alicyclic hydrocarbon radical having 3 to 6 carbon atoms, and includes, for example, cycloalkyl such as cyclopropyl, cyclobutyl, cyclopentyl and cyclohexyl; and cycloalkenyl such as cyclopentenyl and cyclohexenyl.

The term "alkyl" refers to an alkyl group which may be straight chain or branched chain, and includes, for example, methyl, ethyl, n-propyl, iso-propyl, n-butyl, iso-butyl, sec-butyl, tert-butyl, n-pentyl and n-hexyl.

The term "cycloalkyl" is a cyclic alkyl radical, and includes, for example, cyclopropyl, cyclobutyl, cyclopentyl and cyclohexyl.

The substituent(s) for the "optionally substituted phenyl" include, for example, halogen and C$_{1-4}$ alkyl. Said phenyl can be substituted by at least 1, preferably 1 to 2 of these substituent(s).

With regard to the phrase "optionally substituted ring which is formed together with the N-atom", said ring is a 5- to 6-membered monocyclic or benzo-condensed polycyclic heterocyclic ring containing at least 1, preferably only 1 N-atom. Examples of the cyclic rings which may be formed by

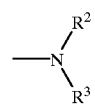

in formula (I) include 1,2-dihydroquinolin-1-yl and 1,2,3,4-tetrahydroquinolin-1-yl. These rings may optionally be substituted and the possible substituents include, for example, C$_{1-4}$ alkyl such as methyl or ethyl and halogen such as fluoro or chloro, preferably being methyl or fluoro.

Preferred compounds of the formula (I) according to the invention are those wherein
R$^1$ represents a 5-membered heterocyclic radical which has one or two N atoms and one O atom or one S atom; two N atoms; or one N atom or O atom and which is optionally substituted by chloro and/or methyl, or represents oxiran-2-yl, chloro-substituted pyridyl, C$_{1-3}$ alkylthio, methylsulfinyl, methylsufonyl, cyclopropyl, cyclopentenyl or cyclohexyl, $R^2$ and $R^3$ represent, independently of one another, $C_{1-4}$ alkyl, $C_{5-6}$ cycloalkyl or optionally substituted phenyl (here the substituent(s) being halogen or $C_{1-4}$ alkyl), or $R^2$ and $R^3$ may form, together with the N-atom to which they are bonded, optionally substituted 1,2-dihydroquinolin-1-yl or 1,2,3,4-tetrahydroquinolin-1-yl (here the substituent(s) being methyl or fluoro), $R^4$ represents a hydrogen atom, and n represents 0 or 1.

More preferred compounds of the formula (I) according to the invention are those wherein $R^1$ represents isooxazolyl, pyrazolyl, 1,2,5-oxadiazolyl, 1,3,4-oxadiazolyl, thiazolyl, isothiazolyl, thienyl or furyl, said radicals optionally being substituted by chloro and/or methyl, or represents oxiran-2-yl, 3-pyridyl, 6-chloro-3-pyridyl, methydtrio, n-propylthio, isopropylthio, methylsulfinyl, methysulfonyl, cyclopropyl, cyclopentenyl or cyclohexyl, $R^2$ and $R^3$ represent, independently of one another, $C_{1-3}$ alkyl, cyclohexyl or optionally substituted phenyl (here the substituent(s) being fluoro, chloro, bromo or methyl), or $R^2$ and $R^3$ may form, together with the N-atom to which they are bonded, 6-fluoro-2,2-dimethyl-1,2,3,4-tetrahydroquinolin-1-yl, 2-methyl-1,2,3,4-tetrahydroquinolin-1-yl, 2,2-dimethyl-1,2-dihydroquinolin-1-yl, 6-fluoro-2,2-dimethyl-1,2-dihydroquinolin-1-yl or 2,2-dimethyl-1,2,3,4-tetrahydroquinolin-1-yl, $R^4$ represents a hydrogen atom, and n represents 0 or 1.

The process (a) for the preparation of the compounds of the above formula (I) is represented by the following equation, when, as the starting materials, for example, 1-(3-isooxazolylmethyl)-5(4H)-tetrazolinone and N-isopropyl-N-phenylcarbamoyl chloride are used.

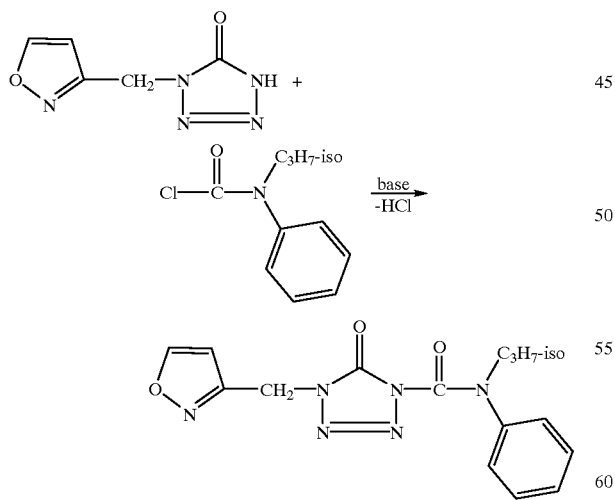

In the above process (a), the compounds of the formula (II) which are used as the starting material are new and can be produced, for instance, by any of the following processes (b) to (f): That is to say by process (b):

the process of reacting compounds of the formula (IV)

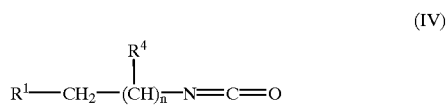

(IV)

wherein $R^1$, $R^4$ and n are as defined above, with trimethylsilyl azide in the presence of a catalytic amount of boron trifluoride-ether complex, or process (c):

the process of reacting the compounds of the above formula (IV) with sodium azide in the presence of a catalytic amount of ammonium chloride in a polar solvent, or process (d):

the process of reacting compounds of the formula (V)

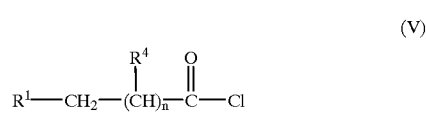

(V)

wherein $R^1$, $R^4$ and n are as defined above, with trimethylsilyl azide in the presence of a catalytic amount of boron trifluorideether complex, or process (e):

the process of reacting compounds of the formula (VI)

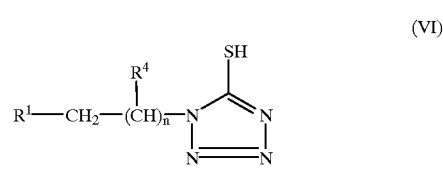

(VI)

wherein $R^1$, $R^4$ and n are as defined above, with compounds of the formula (VII)

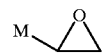

(VII)

wherein

M represents a hydrogen atom or methyl, or process (f): when $R^1$ represents a radical other than $C_{1-4}$ alkyl-S(O)$_m$—, the process of reacting compounds of the formula (VIII)

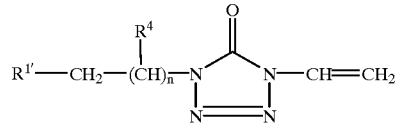

(VIII)

wherein $R^{1'}$ represents the radical as defined for $R^1$, with the exception of $C_{1-4}$ alkyl-S(O)$_m$—, and $R^4$ and n are as defined above,
with sodium periodate in the presence of a catalytic amount of osmium oxide [$OsO_4$].

Alternatively, the compounds of the formula (I) wherein $R^1$ represents alkyl($C_{1-4}$)sulfinyl or alkyl($C_{1-4}$)sulfonyl, can be produced by oxidizing the compound wherein $R^1$ corresponds to alkyl($C_{1-4}$)thio according to a general oxidation method to thereby easily obtain the compound having the corresponding alkyl($C_{1-4}$)sulfinyl or the compounds having the corresponding alkyl($C_{1-4}$)sulfonyl.

Alternatively, the compounds of the formula (I) wherein $R^1$ represents oxiran-2-yl can be obtained by oxidizing 1-(2-propenyl)-4-(N,N-disubstituted carbamoyl)-5(4H)-tetrazolinone with m-chloroperoxybenzoic acid as shown by the later-described Synthesis Example 5, and the compounds of the formula (I) wherein $R^1$ represents 3-methyl-2-isoxazolin-5-yl can preferably be obtained by a conventional method described in Houben-Weyl, 1985, vol. E5, pp. 1591–1610, as shown by the later-described Synthesis Example 6, in which the tetrazolinone as the reactant is a known compound described in Japanese Patent Laid-open Hei 8-259547.

In the above processes (b) and (c), the compounds of the formula (IV) used as the starting materials include isocyanates known in the field of organic chemistry and can be synthesized, for example, by the process described in "Shin Jikken Kagaku Koza (New Experimental-Chemistry Course)" edited by Japanese Chemical Society, Vol. 14, pp. 1490 –1503 (published by Maruzen on Dec. 20, 1977).

In the above process (d), the compounds of the formula (V) used as the starting materials also include acid chlorides known in the field of organic chemistry and can be synthesized, for example, by the process described in Shin Jikken Kagaku Koza (New Experimental Chemistry Course)" edited by Japanese Chemical Society, Vol. 14, pp. 1104 –1120 (published by Maruzen on Dec. 20, 1977). For example, they can easily be obtained by reacting carboxylic acids represented by the formula (IX)

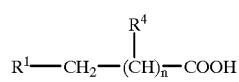

(IX)

wherein
$R^1$, $R^4$ and n are as defined above,
with thionyl chloride as a halogenating agent.

The compounds of the above formula (IX) can be synthesized, for example, by the process described in "Shin Jikken Kagaku Koza (New Experimental Chemistry Course)" edited by Japanese Chemical Society, Vol. 14, pp. 921 –1000 (published by Maruzen on Dec. 20, 1977), or by hydrolyzing the corresponding carboxylic acid esters.

In the above process (e), the compounds of the above formula (VI) can be synthesized, for example, by reacting compounds of the formula (XI)

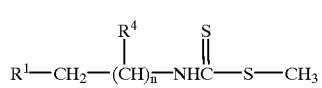

(XI)

wherein
$R^1$, $R^4$ and n are as defined above,
with sodium azide, according to the process described in Berichte, Vol. 28, pp. 74–76 (1895).

The dithiocarbamic acid esters of the above formula (XI) can easily be obtained, for example, by reacting methanethiol with compounds of the formula (XII)

(XII)

wherein
$R^1$, $R^4$ and n are as defined above,
or by reacting compounds of the formula (XIII)

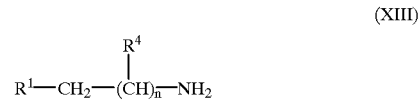

(XIII)

wherein
$R^1$, $R^4$ and n are as defined above,
with carbon disulfide, and further reacting with a methylating, agxent such as dimethyl sulfate or iodomethane.

The compounds of the above formula (XII) can be produced by, for example, the process described in "Shin Jikken Kagaku Koza (New Experimental Chemistry Course)" edited by Japanese Chemical Society, Vol. 14, pp. 1503 –1509 (published by Maruzen on Dec. 20, 1977).

The compounds of the above formula (XIII) can also be produced by, for example, the process described in "Shin Jikken Kagaku Koza (New Experimental Chemistry Course)" edited by Japanese Chemical Society, Vol. 14, pp. 1332 –1399 (published by Maruzen on Dec. 20, 1977).

In the above process (e), the compounds of the formula (VII) used as starting materials are known per se and specific examples thereof include ethylene oxide or 1,2-epoxypropane.

In the above process (f), the compounds of the formula (VIII) used as starting materials can easily be obtained by, for example, reacting 1-ethenyl-5(4H)-tetrazolinone with compounds of the formula (XIX)

(XIX)

wherein
$R^1$, $R^4$ and n are as defined above, and
Hal represents halogen.

The 1-ethenyl-5(4H)-tetrazolinone used in the above reaction is a compound known per se and the compounds of the formula (XIX) are also well known in the field of organic chemistry.

Typical examples of the compounds of the formula (II) are as follows:
1-(1-cyclopentenylmethyl)-5(4H)-tetrazolinone,
1-(2-tetrahydrofurfuryl)-5(4H)-tetrazolinone,
1-(5-methyl-3-isooxazolylmethyl)-5(4H)-tetrazolinone,
1-(3-isooxazolylmethyl)-5(4H)-tetrazolinone,
1-(3,5-dimethyl-4-isooxazolylmethyl)-5(4H)-tetrazolinone,
1-(5-chloro-1,3-dimethyl-4-pyrazolylmethyl)-5(4H)-tetrazolinone,
1-(5-isooxazolylmethyl)-5(4H)-tetrazolinone,
1-(4-methyl-1,2,5-oxadiazol-3-ylmethyl)-5(4H)-tetrazolinone, 1-(4-chloro-5-isoxazolylmethyl)-5(4H)-tetrazolinone,
1-(5-methyl-1,3,4-oxadiazol-2-ylmethyl)-5(4H)-tetrazolinone,
1-[2-(3-methylisoxazol-5-yl)-ethyl]-5(4H)-tetrazolinone,
1-[1-(3-methylisoxazol-5-ylmethyl)-ethyl]-5(4H)-tetrazolinone,
1-(cyclohexylmethyl)-5(4H)-tetrazolinone,
1-(cyclopropylmethyl)-5(4H)-tetrazolinone,
1-(6-chloro-3-pyridylmethyl)-5(4H)-tetrazolinone,
1-(4-thiazolylmethyl)-5(4H)-tetrazolinone,
1-(4-isothiazolylmethyl)-5(4H)-tetrazolinone,
1-methylthiomethyl-5(4H)-tetrazolinone,
1-n-propylthiomethyl-5(4H)-tetrazolinone, etc.

On the other hand, the compounds of the formula (III) which are reacted with the compounds of the above formula (II) are carbamoyl chlorides which are well known in the field of organic chemistry. Typical examples thereof are as follows:
N,N-diethylcarbamoyl chloride,
N-cyclohexyl-N-ethylcarbamoyl chloride,
N,N-di-isopropylcarbamoyl chloride,
N-ethyl-N-isopropylcarbamoyl chloride,
N-methyl-N-isopropylcarbamoyl chloride,
N-isopropyl-N-phenylcarbamoyl chloride,
N-4-fluorophenyl-N-isopropylcarbamoyl chloride,
N-4-chlorophenyl-N-isopropylcarbamoyl chloride,
N-isopropyl-N-p-tolylcarbamoyl chloride,
N-4-bromophenyl-N-isopropylcarbamoyl chloride,
2,2-dimethyl-1,2,3,4-tetrahydroquinolin-1-yl carbonyl chloride,
2-methyl-1,2,3,4-tetrahydroquinolin-1-yl carbonyl chloride,
N-ethyl-N-phenylcarbamoyl chloride,
N-n-propyl-N-phenyl carbamtoyl chloride,
N-cyclohexyl-N-isopropylcarbamoyl chloride,
2,2-dimethyl-1,2-dihydroquinolin-1-yl carbonyl chloride,
6-fluoro-2,2-dimethyl-1,2-dihydroquinolin-1-yl carbonyl chloride,
6-fluoro-2,2-dimethyl-1,2,3,4-tetrahydroquinolin-1-yl carbonyl chloride, etc.

The reaction in the process (a) may usually be carried out in an organic solvent which is inert to the reaction. Examples of the inert organic solvents useful for the reaction include aliphatic, alicyclic and aromatic hydrocarbons (which may optionally be chlorinated) such as pentane, hexane, cyclohexane, petroleum ether, ligroin, benzene, toluene, xylene, dichloromethane, chloroform, carbon tetrachloride, 1,2-dichloroethane, chlorobenzene and dichlorobenzene; ethers such as diethyl ether, methyl ethyl ether, di-isopropyl ether, dibutyl ether, dioxane, dimethoxyethane (DNE), tetrahydrofuran (THF) and diethyleneglycol dimethyl ether (DGM); nitrites such as acetonitirile and propionitrile; acid amides such as dimethylformamide (DMF), dimethylacetamide(DMA), N-methylpyrrolidone, 1,3-dimethyl-2-imidazolidinone and hexamethylphosphoric triamide (HMPA); and others.

The process (a) can be carried out in the presence of a base and the preferred examples of the useful bases include 4-dimethylaminopyridine (DMAP).

In the case of using DMAP as a base, the reaction in the process (a) can be carried out generally under a normal pressure at a temperature of about −10 to about 200° C., preferably about 25 to about 140° C., but it may also be optionally operated under an elevated or reduced pressure.

Further, the reaction in the process (a) can also be carried out using bases other than DMAP and such bases are exemplified by inorganic salts (such as sodium carbonate, potassium carbonate, sodium hydroxide, potassium hydroxide, etc.), alkylalcoholates (such as sodium methoxide, sodium ethoxide, potassium-tert-botoxide, etc.), sodium hydroxide; potassium hydroxide; lithium hydroxide; organic bases (such as triethylamine, 1,1,4,4-tetramethylethylenediamine, N,N-dimethylaniline, pyridine, etc.); and others.

In the case of carrying out the reaction by use of such bases, the compound of the formula (I) can selectively be obtained by using DMAP as a catalyst.

The reaction temperature in this reaction is generally within a range of about 0 to about 150° C., preferably about 25 to about 100° C. The reaction should preferably be carried out under a normal pressure, but it may also be optionally operated under an elevated or reduced pressure.

Thereupon, the compound of the formula (I) can be obtained by, for example, reacting about 1 to about 1.5 moles of the compound of the formula (III) with 1 mole of the compound of the formula (II) in the presence of about 1 to about 1.5 moles of DMAP as a base, in the inert solvent as mentioned above. Alternatively, the compound of the formula (I) can also be obtained by reacting about 1 to about 1.5 moles of the compound of the formula (III) with 1 mole of the compound of the formula (II) in the presence of about 0.01 to about 0.3 mole of DMAP as a catalyst and about 1 to about 1.5 moles of a base, for instance, potassium carbonate, in the inert solvent as mentioned above.

The compound of the formula (I) thus produced can be isolated and purified by means of, for instance, crystallization, chromatography and the like.

On the other hand, the above process (b) can be conducted using boron trifluoride ethyl ether complex as a catalyst. The reaction temperature may be set up to generally about 0 to about 200° C., preferably about 50 to about 150° C. Further, the reaction should preferably be carried out under a normal pressure, but it may also be optionally operated under an elevated or reduced pressure.

The process (b) can be conducted by reacting about 1 to about 2 moles of trimethylsilyl azide with 1 mole of the compound of the formula (IV) in the presence of about 0.005 to about 0.01 mole of boron trifluoride ethyl ether complex as a catalyst.

Further, the reaction in the process (c) can be carried out usually in a polar solvent and the useful polar solvents are exemplified by acid amides such as dimethylformamide, dimethylacetamide, etc.; and sulfoxides such as dimethylsulfoxide, sulfolane, etc. The reaction temperature is generally about 0 to about 200° C., preferably about 20 to about 150° C. The reaction should preferably be carried out under a normal pressure, but it may also be optionally operated under an elevated or reduced pressure.

The process (c) can generally be conducted by reacting about 1 to about 1.5 moles of sodium azide with 1 mole of the compound of the formula (IV) in the presence of about 0.05 to about 1 mole of aluminum chloride as a catalyst, in a polar solvent such as dimethylformamide.

The reaction in the process (d) can be carried out generally under a normal pressure at a temperature of about 0 to about 200° C., preferably about 25 to about 130° C., but it may also be optionally operated under an elevated or reduced pressure.

The process (d) can be conducted by reacting about 2 to about 4 moles of trimethylsilyl azide with 1 mole of the compound of the formula (V).

The reaction in the process (e) may usually be carried out in a solvent which is inert to the reaction. Examples of the inert solvents useful for the reaction include, for example, water; and alcohols (such as methanol, ethanol and isopropanol).

The reaction in the process (e) can be carried out in the presence of a base, for example, inorganic bases (such as sodium hydrogencarbonate, potassium hydrogencarbonate, sodium carbonate, potassium carbonate, sodium hydroxide and potassium hydroxide).

The reaction temperature in the process (e) can be set up to usually about −30 to about 50° C., preferably about 0 to about 30° C. Further, the reaction should preferably be carried out under a normal pressure, but it may also be optionally operated under an elevated or reduced pressure.

The process (e) can be conducted by reacting about 1 to about 1.3 moles of the compound of the formula (VII) with 1 mole of the compound of the formula (VI) in the presence of a base in an inert solvent.

The reaction in the process (f) may usually be carried out in a solvent which is inert to the reaction. Examples thereof include, for example, water; alcohols (such as ethanol); ethers (such as dioxane) and carbon tetrachloride.

The reaction temperature in the process (f) is usually about −30 to about 50° C., preferably about 0 to about 40° C. The reaction should preferably be carried out under a normal pressure, but it may also be optionally operated under an elevated or reduced pressure.

The process (f) can be conducted by reacting about 2 to about 3 moles of sodium periodate with 1 mole of the compound of the formula (VIII) in the presence of a catalytic amount of osmium oxide [$OsO_4$].

The active compounds of formula (I) according to the invention have, as shown in the test examples afterward, excellent herbicidal activity so that they can be used as agrochemicals, particularly herbicides for controlling weeds. The term "weeds" means all plants which grow in undesired loci.

The compounds according to the invention act as non-selective or selective herbicides in dependence on the concentration used.

The active compounds according to the invention can be used, for example, as selective herbicides in connection with the following weeds and the cultivated plants.

Dicotyledon weeds of the genera: Sinapis, Lepidium, Galium, Stellaria, Chenopodium, Urtica, Senecio, Amaranthus, Portulaca, Xanthium, Ipomoea, Polygonum, Ambrosia, Cirsium, Sonchus, Solanum, Rorippa, Lamium, Veronica, Datura, Viola, Galeopsis, Papaver, Centaurea, Galinsoga, Rotala, Lindernia, etc.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita, etc.

Monocotyledon weeds of the genera: Echinochloa, Setaria, Panicum, Digitaria, Phleum, Poa, Festuca, Eleusine, Lolium, Bromus, Avena, Cyperus, Sorghum, Agropyron, Monochoria, Fimbristylis, Sagittaria, Eleocharis, Scirpus, Paspalum, Ischaemum, Agrostis, Alopecurus, Cynodon, etc.

Monocotyledon cultures of the genera: Oryza, Zea, Triticum, Hordeum, Avena, Secale, Sorghum, Panicum, Saccharum, Ananas, Asparagus, Allium, etc.

However, the use of the active compounds of the formula (I) according to the invention is in no way restricted to the above genera, but also extends in the same manner to other plants. Further, the active compounds of the invention are suitable, depending on the concentration, for the total combating of weeds, for example on industrial terrain, rail tracks, and on paths and squares with or without tree plantings.

Equally, the active compounds of the invention can be employed for combating weeds in perennial cultures, for example afforstations decorative tree plantations, orchards, vineyards, citrus groves, nuts orchards, banana plantations, coffee plantations, tea plantations, rubber plantations, oil palm plantations, cocoa plantations, soft fruit and plantations and hopfields, and for the selective combating of weeds in annual cultures.

The active compounds of the formula (I) according to the invention can be converted to the customary formulations, such as solutions, emulsions, wettable powders, suspensions, powders, soluble powders, granules, tablets, suspension-emulsion concentrates, very fine capsules in polymeric substances, natural and synthetic materials impregnated with active compound, etc.

These formulations are produced in the manner known per se, for example, by mixing the active compounds with extenders, such as liquid solvents and/or solid carriers, optionally with the use of surface-active agents, such as emulsifying agents and/or dispersing agents and/or foam-forming agents.

Suitable liquid solvents include: aromatic hydrocarbons, such as xylene, toluene or alkyl naphthalenes; chlorinated aromatic hydrocarbons and chlorinated aliphatic hydrocarbons, such as chlorobenzenes, chloroethylenes or methylene chloride; aliphatic hydrocarbons, such as cyclohexane or paraffins, for example petroleum fractions, mineral and vegetable oils; alcohols, such as butanol or glycol as well as their ethers and esters, ketones, such as acetone, methyl ethyl ketone, methyl isobutyl ketone or cyclohexanone; strongly polar solvents, such as dimethylformamide and dimethylsulfoxide; as well as water. When water is used as an extender, organic solvents can be used as auxiliary solvents.

Suitable solid carriers include: ammonium salts and ground natural minerals, such as kaolins, clays, talc, chalk, quartz, attapulgite, montmorillonite or diatomaceous,earth, and ground synthetic minerals, such as highly disperse silicic acid, alumina and silicates. Suitable solid carriers for granules include: for example, crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

Suitable emulsifying and/or foam-forming agents include: for example non-ionic and anionic emulsifiers, such as polyoxyethylene-fatty acid esters, polyoxyethylene-fatty alcohol ethers, for example alkylaryl polyglycol ethers, alkylsulfonates, alkylsulfates, arylsulfonates as well as albumin hydrolysation products.

Suitable dispersing agents include: for example lignin-sulphite waste liquors and methylcellulose.

Adhesives may also be optionally used in formulations include powders, granules, natural and synthetic materials impregnated with active compound or emulsions. The following are examples of such adhesives: carboxymethylcellulose and natural and synthetic polymers such as gum arabic, polyvinyl alcohol and polyvinyl acetate, as well as natural phospholipids, such as cephalins and lecithins, synthetic phospholipids. Additionally, mineral and vegetable oils can also be used as further additives.

It is possible to use colorants such as inorganic pigments, for example iron oxide, titanium oxide and Prussian Blue; and organic dyestuffs, such as alizarin dyestuffs, azo dyestuffs and metal phthalocyanine dyestuffs, and trace nutrients such as salts of metals, for example iron, manganese, boron, copper, cabalt, molybdenum and zinc.

The formulations in general contain between 0.1 and 95 per cent by weight preferably between 0.5 and 90% by weight of the active compound.

The active compounds of the invention can be used for controlling of weeds as they are or in a form of such formulations and can be mixed with any of known herbicides. The mixture may be either prepared in advance in the form of a final formulation or prepared by tank-mixing immediately before use.

It is possible to mix the active compounds of the formula (I) according to the invention with a chemical injury-mitigating agent and thus broading the applicability of the instant compounds as a selective herbicide.

The chemical injury-mitigating agent may be exemplified by 1-(α,α-dimethylbenzyl)-3-p-tolyl urea.

The active compounds of the formula (I) according to the invention may be applied as they are or in the above form of the formulations, by any of conventional methods such as watering, spraying, atomizing, powder spreading or granule scattering.

The active compounds of the formula (I) according to the invention may be applied at any stage of preemergence or postemergence. Also, they can be incorporated into the soil before sowing.

The application amount of the active compound is not strictly limited and may be varied within a wide range depending on the desired effect, the kind of target plant(s) as the object, the location of application, the time of application and the like but, as a tentative measure, for example, the amount can be exemplified by about 0.001 kg/ha to about 10 kg/ha, preferably about 0.01 kg/ha to about 5 kg/ha of the active compound.

The following examples illustrate the production and uses of the inventive compounds, but they should not be regarded as limiting the invention in any way. The term "part(s)" therein means "part(s) by weight" unless otherwise noted.

EXAMPLES

Synthesis Example 1

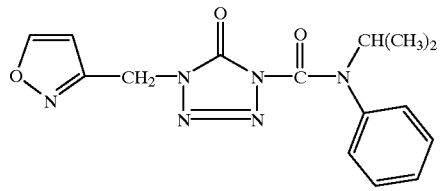

0.6 g of 1-(3-isooxazolylmethyl)-5(4H)-tetrazolinone, 0.5 g of 4-dimethylamino-pyridine and 0.8 g of N-isopropyl-N-phenylcarbamoyl chloride were suspended in 30 ml of toluene and the suspension was stirred for 5 hours at 50–55° C. After allowing to cool off, the organic layer was washed successively with water, 1N hydrochloric acid, water and brine. After drying the organic layer over anhydrous sodium sulfate, the solvent was distilled off under reduced pressure and the residue was purified by column chromatography (ethanol/chloroform=2/100) to obtain 1.0 g of 1-(3-isoxazolylmethyl)-4-N-isopropyl-N-phenylcarbamoyl)-5 (4H)-tetrazolinone. m.p.: 110–112° C.

Synthesis Example 2

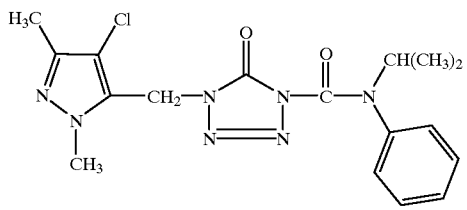

0.4 g of 1-(4-chloro-1,3)-dimethyl-5-pyrazolylmethyl)-5 (4H)-tetrazolinone, 0.26 g, of 4-dimethylaminopyridini and 0.41 g of N-isopropyl-N-phenylcarbamoyl chloride were suspended in 50 ml of toluene and the suspension was stirred for 5 hours at 50–55° C. After allowing to cool off, the organic layer was washed successively with water, 1N hydrochloric acid, water and brine. After drying the organic layer over anhydrous sodium sulfate, the solvent was distilled off under reduced pressure and the residue was purified by column chromatography (ethanol/chloroform=2/150) to obtain 0.6 g of 1-(4-chloro-1,3-dimethyl-5-pyrazolylmethyl)-4-(N-isopropyl-N-phenylcarbamoyl)-5 (4H)-tetrazolinone. m.p.: 158–159.5° C.

Synthesis Example 3

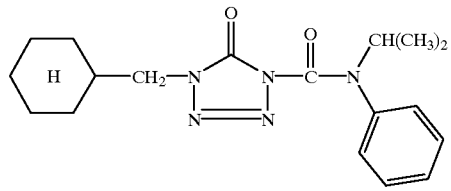

0.6 g of 1-cyclohexylmethyl-5(4H)-tetrazolinone, 0.45 g of 4-dimethylaminopyridine and 0.72 g of N-isopropyl-N-phenylcarbamoyl chloride were suspended in toluene and the suspension was stirred for 5 hours at 50–55° C. After allowing to cool off, the organic layer was washed successively with water, 1N hydrochloric acid and brine. After drying the organic layer over anhydrous sodium sulfate, the solvent was distilled off under reduced pressure and the residue was purified by column chromatography (chloroform: 100%) to obtain 0.9 g of 1-cyclohexylmethyl-4-(N-isopropyl-N-phenylcarbamoyl)-5(4H)-tetrazolinone. m.p.: 79–81.5° C.

Synthesis Example 4

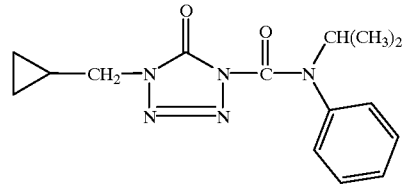

0.7 g of 1-cyclopropylmethyl-5(4H)-tetrazolinone, 0.8 g of 4-dimethylaminopyridine and 0.8 g of N-isopropyl-N-phenylcarbamoyl chloride were suspended in toluene and the suspension was stirred for 6 hours at 50–55° C. After-allowing to cool off, the organic layer was washed successively with water, diluted hydrochloric acid and brine and dried over anhydrous magnesium sulfate. The solvent was distilled off under reduced pressure and the residue was purified by column chromatography on silica gel (chloroform) to obtain 1.4 g of 1-cyclopropylmethyl-4-(N-isopropyl-N-phenylcarbaroyl)-5(4H)-tetrazolinone. m.p.: 67–69° C.

Table 1 shows the compounds of the formula (I) according to the invention obtained in the same manner as those of the above Synthesis Examples 1–4, together with the compounds obtained in the above Synthesis Examples 1–4.

TABLE 1

(I)

$$R^1-CH_2-(CH)_n-N\underset{N=N}{\overset{R^4}{\underset{|}{\big|}}}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!$$

| Compound No. | $R^1$ | $(CH)_n$ with $R^4$ | $R^2$ | $R^3$ (on N) | m.p. (° C.) or $n_D^{20}$ |
|---|---|---|---|---|---|
| 1 | isoxazol-3-yl | — | $C_3H_7$-iso | phenyl | 110–112 |
| 2 | isoxazol-3-yl | — | $C_3H_7$-iso | 4-F-phenyl | 1.5276 |
| 3 | isoxazol-3-yl | — | $C_3H_7$-iso | 4-Cl-phenyl | |
| 4 | isoxazol-3-yl | — | $C_3H_7$-iso | 4-Br-phenyl | |
| 5 | isoxazol-3-yl | — | $C_3H_7$-iso | 4-CH$_3$-phenyl | |
| 6 | isoxazol-3-yl | — | \multicolumn{2}{l}{2-methyl-1,2,3,4-tetrahydroquinolin-1-yl} | 111–115.5 |
| 7 | isoxazol-3-yl | — | \multicolumn{2}{l}{2,2-dimethyl-1,2-dihydroquinolin-1-yl} | |
| 8 | isoxazol-3-yl | — | \multicolumn{2}{l}{2,2-dimethyl-6-fluoro-1,2-dihydroquinolin-1-yl} | |
| 9 | isoxazol-3-yl | — | $C_2H_5$ | phenyl | |

TABLE 1-continued
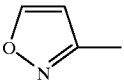
(I)
| Compound No. | R¹ | R⁴ (CH)ₙ | R² | —(N)—R³ | m.p. (° C.) or $n_D^{20}$ |
|---|---|---|---|---|---|
| 10 | 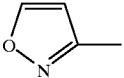 | — | $C_2H_5$ | $C_3H_7$-iso | |
| 11 | 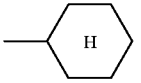 | — | $C_2H_5$ | 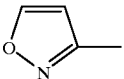 | |
| 12 | 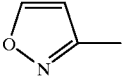 | — | $CH_3$ | $C_3H_7$-iso | |
| 13 | 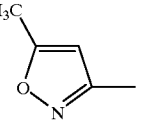 | — | $C_2H_5$ | $C_2H_5$ | |
| 14 | 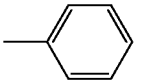 | — | $C_3H_7$-iso | 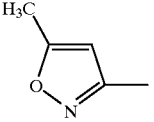 | 84–86 |
| 15 |  | — | $C_3H_7$-iso | 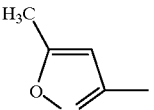 | 106–109 |
| 16 | 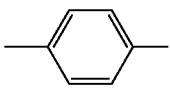 | — | $C_3H_7$-iso | 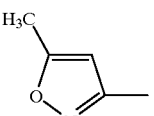 | |
| 17 | 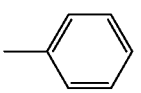 | — | $C_2H_5$ | 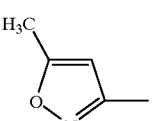 | |
| 18 | 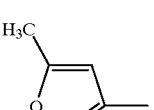 | — | $C_2H_5$ | $C_3H_7$-iso | 1.5012 |
| 19 | 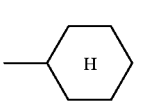 | — | $C_2H_5$ | 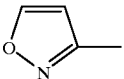 | |

TABLE 1-continued (I)

$R^1-CH_2-(CH)_n-N-N-C-N{R^2 \atop R^3}$ (tetrazolinone core with R⁴ on CH)

| Compound No. | R¹ | R⁴ (CH)ₙ | R² | R³ | m.p. (° C.) or $n_D^{20}$ |
|---|---|---|---|---|---|
| 20 | 3,5-dimethylisoxazol-4-yl (H₃C, CH₃ on isoxazole) | — | C₂H₅ | C₂H₅ | |
| 21 | 3,4,5-trimethylisoxazol-4-yl | — | C₃H₇-iso | phenyl | 88–92 |
| 22 | 3,4,5-trimethylisoxazol-4-yl | — | C₃H₇-iso | 4-F-phenyl | |
| 23 | 3,4,5-trimethylisoxazol-4-yl | — | C₃H₇-iso | 4-Cl-phenyl | |
| 24 | 3,4,5-trimethylisoxazol-4-yl | — | C₃H₇-iso | 4-CH₃-phenyl | |
| 25 | 3,4,5-trimethylisoxazol-4-yl | — | C₂H₅ | phenyl | |
| 26 | 3,4,5-trimethylisoxazol-4-yl | — | C₂H₅ | C₂H₅ | |

TABLE 1-continued (I)

$$R^1-CH_2-(CH)_n-N-N-C-N-R^2/R^3$$ (structure with tetrazolinone core, R⁴ on CH)

| Compound No. | R¹ | R⁴/(CH)ₙ | R² | —(N)— R³ | m.p. (° C.) or $n_D^{20}$ |
|---|---|---|---|---|---|
| 27 | 3,5-dimethyl-4-yl isoxazole (CH₃, CH₃) | — | C₂H₅ | C₃H₇-iso | 1.5037 |
| 28 | 3,5-dimethyl-4-yl isoxazole | — | C₂H₅ | cyclohexyl, H | |
| 29 | 3,5-dimethyl-4-yl isoxazole | — | | 2-methyl-1,2,3,4-tetrahydroquinolin-1-yl (H₃C on C2) | 151.5–152.5 |
| 30 | isoxazol-3-yl | — | C₃H₇-iso | C₆H₅ | 1.5441 |
| 31 | isoxazol-3-yl | — | C₃H₇-iso | 4-F-C₆H₄ | |
| 32 | isoxazol-3-yl | — | C₃H₇-iso | 4-Cl-C₆H₄ | |
| 33 | isoxazol-3-yl | — | C₃H₇-iso | 4-CH₃-C₆H₄ | |
| 34 | isoxazol-3-yl | — | C₂H₅ | C₆H₅ | |
| 35 | isoxazol-3-yl | — | C₂H₅ | C₂H₅ | |
| 36 | isoxazol-3-yl | — | C₂H₅ | C₃H₇-iso | |

TABLE 1-continued
(I)
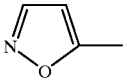
| Compound No. | R¹ | R⁴ (CH)ₙ | R² | —(N)— R³ | m.p. (° C.) or $n_D^{20}$ |
|---|---|---|---|---|---|
| 37 | 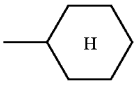 | — | $C_2H_5$ | 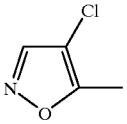 H | |
| 38 | 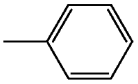 | — | $C_3H_7$-iso | 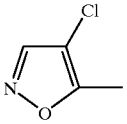 | 112–116.5 |
| 39 |  | — | $C_3H_7$-iso | 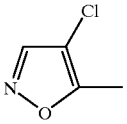 F | |
| 40 |  | — | $C_3H_7$-iso | 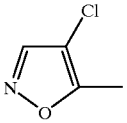 Cl | |
| 41 | 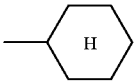 | — | $C_2H_5$ | 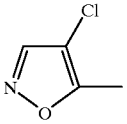 H | |
| 42 | 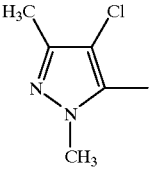 | — | $CH_3$ | $C_3H_7$-iso | |
| 43 | 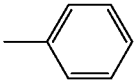 | — | $C_3H_7$-iso | 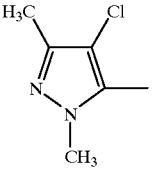 | 158.5–159.5 |
| 44 | 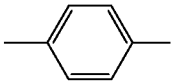 | — | $C_3H_7$-iso |  F | |

TABLE 1-continued (I)

$$R^1-CH_2-(CH)_n\overset{R^4}{-}N-\underset{N=N}{\overset{O}{\underset{\|}{C}}}-N-\overset{O}{\underset{\|}{C}}-N\overset{R^2}{\underset{R^3}{}}$$

| Compound No. | R¹ | R⁴<br>(CH)ₙ | R²—(N)—R³ | | m.p. (° C.)<br>or $n_D^{20}$ |
|---|---|---|---|---|---|
| 45 | 4-Cl-3,5-dimethyl-1-methylpyrazole | — | C₃H₇-iso | 4-Cl-phenyl | |
| 46 | 4-Cl-3,5-dimethyl-1-methylpyrazole | — | C₂H₅ | phenyl | |
| 47 | 4-Cl-3,5-dimethyl-1-methylpyrazole | — | \multicolumn{2}{l|}{1,2-dimethyl-1,2,3,4-tetrahydroquinolin-2-yl} | |
| 48 | 4-Cl-3,5-dimethyl-1-methylpyrazole | — | \multicolumn{2}{l|}{1,2,2-trimethyl-6-fluoro-1,2-dihydroquinolin-2-yl} | |
| 49 | 4-Cl-3,5-dimethyl-1-methylpyrazole | — | C₂H₅ | cyclohexyl | |
| 50 | 5-Cl-1,3,4-trimethylpyrazole | — | C₃H₇-iso | phenyl | 92–97.5 |
| 51 | 5-Cl-1,3,4-trimethylpyrazole | — | C₃H₇-iso | 4-F-phenyl | 119–121.5 |

TABLE 1-continued $$R^1-CH_2-(CH)_n-N\underset{N=N}{\overset{R^4}{\underset{\|}{N}}}\underset{\|}{\overset{O}{\underset{\|}{C}}}-\overset{O}{\underset{\|}{C}}-N\underset{R^3}{\overset{R^2}{\diagup}}$$ (I)

| Compound No. | R¹ | R⁴ (CH)n | R² —(N)— R³ | | m.p. (° C.) or $n_D^{20}$ |
|---|---|---|---|---|---|
| 52 | 1,3-dimethyl-5-chloro-4-methyl-pyrazol-4-yl | — | C₃H₇-iso | 4-Cl-C₆H₄ | |
| 53 | 1,3-dimethyl-5-chloro-4-methyl-pyrazol-4-yl | — | C₂H₅ | C₆H₅ | |
| 54 | 1,3-dimethyl-5-chloro-4-methyl-pyrazol-4-yl | — | 1,2-dimethyl-1,2,3,4-tetrahydroquinolin-2-yl | | |
| 55 | 1,3-dimethyl-5-chloro-4-methyl-pyrazol-4-yl | — | 1,2,2-trimethyl-1,2,3,4-tetrahydroquinolin-2-yl | | |
| 56 | 1,3-dimethyl-5-chloro-4-methyl-pyrazol-4-yl | — | C₂H₅ | C₆H₁₁ | |
| 57 | 3,4-dimethyl-furazan-yl | — | C₃H₇-iso | C₆H₅ | 1.5312 |
| 58 | 3,4-dimethyl-furazan-yl | — | C₃H₇-iso | 4-F-C₆H₄ | |
| 59 | 3,4-dimethyl-furazan-yl | — | C₃H₇-iso | 4-Cl-C₆H₄ | |

TABLE 1-continued
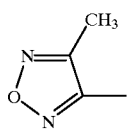
(I)
| Compound No. | R¹ | R⁴ (CH)n | R² —(N)— R³ | | m.p. (° C.) or $n_D^{20}$ |
|---|---|---|---|---|---|
| 60 | 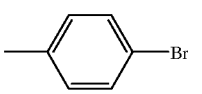 | — | $C_3H_7$-iso | 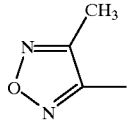 | |
| 61 | 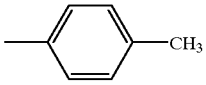 | — | $C_3H_7$-iso | 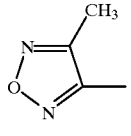 | |
| 62 | 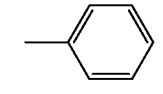 | — | $C_2H_5$ | 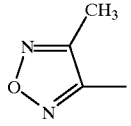 | |
| 63 | 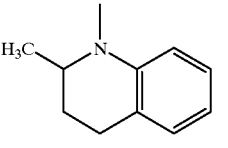 | — | 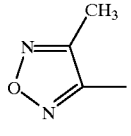 | | |
| 64 | 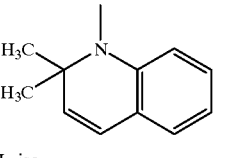 | — | 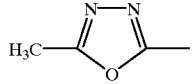 | | |
| 65 | 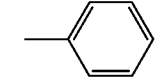 | — | $C_3H_7$-iso | 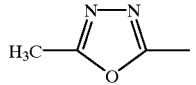 | oily |
| 66 | 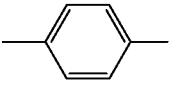 | — | $C_3H_7$-iso | 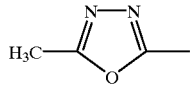 | |
| 67 | 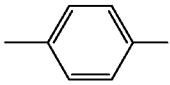 | — | $C_3H_7$-iso | 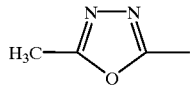 | |
| 68 |  | — | $C_3H_7$-iso | 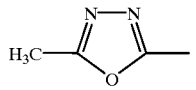 | |
| 69 | 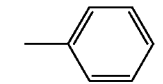 | — | $C_2H_5$ | | |

TABLE 1-continued (I) Structure: R¹—CH₂—(CH)ₙ(R⁴)—N—(tetrazolinone with C=O)—N—C(=O)—N(R²)(R³)

| Compound No. | R¹ | R⁴ (CH)ₙ | R² | —(N)— R³ | m.p. (° C.) or $n_D^{20}$ |
|---|---|---|---|---|---|
| 70 | 2,5-dimethyl-1,3,4-oxadiazole | — | | 1-methyl-2-methyl-1,2,3,4-tetrahydroquinoline | |
| 71 | 2,5-dimethyl-1,3,4-oxadiazole | — | | 1-methyl-2,2-dimethyl-1,2-dihydroquinoline | |
| 72 | 2,5-dimethyl-1,3,4-oxadiazole | — | | 1-methyl-2,2-dimethyl-6-fluoro-1,2-dihydroquinoline | |
| 73 | 2-chloropyridin-5-yl | — | $C_3H_7$-iso | phenyl | 112.5–114.5 |
| 74 | 2-chloropyridin-5-yl | — | $C_3H_7$-iso | 4-fluorophenyl | |
| 75 | 2-chloropyridin-5-yl | — | $C_2H_5$ | $C_2H_5$ | 96–98 |
| 76 | 2-chloropyridin-5-yl | — | | 1-methyl-2-methyl-1,2,3,4-tetrahydroquinoline | |
| 77 | cyclopropyl | — | $C_3H_7$-iso | phenyl | 67–69 |
| 78 | cyclopropyl | — | $C_3H_7$-iso | 4-fluorophenyl | |
| 79 | cyclopropyl | — | $C_3H_7$-iso | 4-chlorophenyl | |
| 80 | cyclopropyl | — | $C_3H_7$-iso | 4-methylphenyl | |

TABLE 1-continued $$\text{(I)}$$

R¹—CH₂—(CH)ₙ—N—C(=O)—N(R²)(R³), tetrazolinone ring with R⁴ on CH

| Compound No. | R¹ | R⁴<br>(CH)ₙ | R² | —(N)— R³ | m.p. (° C.)<br>or $n_D^{20}$ |
|---|---|---|---|---|---|
| 81 | cyclopropyl | — | C₂H₅ | phenyl | |
| 82 | cyclopropyl | — | | 1-methyl-2-methyl-1,2,3,4-tetrahydroquinolin-N-yl | 111–113 |
| 83 | cyclopropyl | — | | 1,2,2-trimethyl-1,2-dihydroquinolin-N-yl | |
| 84 | cyclopropyl | — | | 1,2,2-trimethyl-6-fluoro-1,2-dihydroquinolin-N-yl | |
| 85 | cyclopentenyl | — | C₃H₇-iso | phenyl | 85–85.5 |
| 86 | cyclopentenyl | — | C₃H₇-iso | 4-fluorophenyl | |
| 87 | cyclopentenyl | — | C₃H₇-iso | 4-chlorophenyl | |
| 88 | cyclopentenyl | — | C₃H₇-iso | 4-methylphenyl | |
| 89 | cyclopentenyl | — | C₂H₅ | phenyl | |
| 90 | cyclopentenyl | — | | 1-methyl-2-methyl-1,2,3,4-tetrahydroquinolin-N-yl | |

TABLE 1-continued $$\text{(I)}\quad R^1-CH_2-(CH)_n-N-\underset{\underset{N=N}{|}}{\overset{\overset{O}{\|}}{C}}-N\overset{R^2}{\underset{R^3}{\diagdown}}$$

| Compound No. | R¹ | R⁴<br>(CH)ₙ | R² | —(N)— R³ | m.p. (° C.)<br>or $n_D^{20}$ |
|---|---|---|---|---|---|
| 91 | cyclopentenyl-CH₂- | — | | 1-N-methyl-2,2-dimethyl-1,2-dihydroquinoline | |
| 92 | cyclopentenyl-CH₂- | — | | 1-N-methyl-2,2-dimethyl-6-fluoro-1,2-dihydroquinoline | |
| 93 | tetrahydrofuran-2-yl-CH₂- | — | C₃H₇-iso | phenyl | 1.5303 |
| 94 | tetrahydrofuran-2-yl-CH₂- | — | C₃H₇-iso | 4-fluorophenyl | |
| 95 | tetrahydrofuran-2-yl-CH₂- | — | C₂H₅ | cyclohexyl | |
| 96 | tetrahydrofuran-2-yl-CH₂- | — | | 1-N-methyl-2-methyl-1,2,3,4-tetrahydroquinoline | |
| 97 | tetrahydrofuran-2-yl-CH₂- | — | | 1-N-methyl-2,2-dimethyl-1,2-dihydroquinoline | |
| 98 | cyclopropyl-CH₂- | — | C₂H₅ | cyclohexyl | |
| 99 | cyclopentenyl-CH₂- | — | C₂H₅ | cyclohexyl | |
| 100 | cyclohexyl-CH₂- | — | C₃H₇-iso | phenyl | 79–81.5 |
| 101 | cyclohexyl-CH₂- | — | C₃H₇-iso | 4-fluorophenyl | |

TABLE 1-continued
$$\underset{R^1-CH_2-(CH)_n-N}{\overset{R^4}{\underset{N=N}{\bigvee}}}\overset{O}{\underset{N=N}{\bigvee}}\overset{O}{\underset{R^3}{\overset{R^2}{\bigvee}}}\quad(I)$$
| Compound No. | R¹ | $\overset{R^4}{(CH)_n}$ | R²—(N)—R³ | | m.p. (°C.) or $n_D^{20}$ |
|---|---|---|---|---|---|
| 102 | 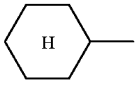 | — | C₃H₇-iso | 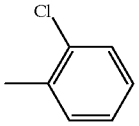 | 1.5329 |
| 103 | 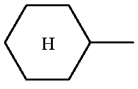 | — | C₃H₇-iso | 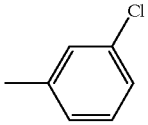 | 92.5–95.5 |
| 104 | 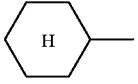 | — | C₃H₇-iso | 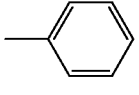 | 69–72.5 |
| 105 | 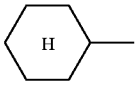 | — | C₃H₇-iso | 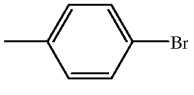 | |
| 106 | 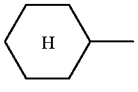 | — | C₃H₇-iso | 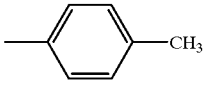 | 83.5–85 |
| 107 | 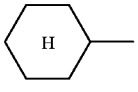 | — | C₂H₅ | 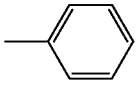 | |
| 108 | 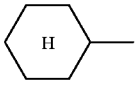 | — | C₂H₅ | 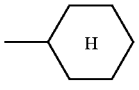 | 1.5023 |
| 109 | 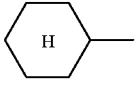 | — | C₃H₇-iso | 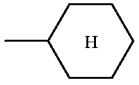 | |
| 110 | 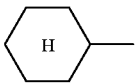 | — | CH₃ | 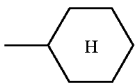 | |
| 111 | 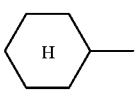 | — | C₂H₅ | C₂H₅ | |
| 112 | 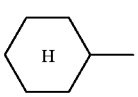 | — | C₂H₅ | C₃H₇-iso | |

TABLE 1-continued $$\text{(I)}$$

Structure: R¹—CH₂—(CH)ₙ(R⁴)—N—N(C=O)—N(C=O—NR²R³)—N=N (tetrazolinone ring)

| Compound No. | R¹ | R⁴(CH)ₙ | R² | —(N)— R³ | m.p. (° C.) or $n_D^{20}$ |
|---|---|---|---|---|---|
| 113 | 3-pyridyl-CH₂ | — | C₃H₇-iso | phenyl | |
| 114 | 2-thienyl-CH₂ | — | C₃H₇-iso | phenyl | |
| 115 | 4-thiazolyl-CH₂ | — | C₃H₇-iso | phenyl | |
| 116 | 3-isothiazolyl-CH₂ | — | C₃H₇-iso | phenyl | |
| 117 | CH₂S | CH₂ | C₃H₇-iso | phenyl | 62–66 |
| 118 | CH₂S | — | C₃H₇-iso | phenyl | 1.5485 |
| 119 | CH₂S | — | C₃H₇-iso | 4-F-phenyl | 1.5333 |
| 120 | CH₃S(O) | — | C₃H₇-iso | phenyl | 1.5453 |
| 121 | CH₃SO₂ | — | C₃H₇-iso | phenyl | 84–87 |
| 122 | n-C₃H₇S | — | C₃H₇-iso | phenyl | 54–54.5 |
| 123 | iso-C₃H₇S | — | C₃H₇-iso | phenyl | 1.5387 |
| 124 | C₂H₅S | — | C₃H₇-iso | phenyl | |

TABLE 1-continued (I)

R¹—CH₂—(CH)ₙ—N(R⁴)—(tetrazolinone ring)—C(O)—N(R²)(R³)

| Compound No. | R¹ | (CH)ₙ with R⁴ | R² | —(N)— R³ | m.p. (° C.) or $n_D^{20}$ |
|---|---|---|---|---|---|
| 125 | epoxide (oxirane) | — | $C_3H_7$-iso | phenyl | 1.5289 |
| 126 | 3-methyl-2-isoxazolin-5-yl | CH₂ | $C_3H_7$-iso | phenyl | 76.5–79.5 |
| 127 | 3-methyl-2-isoxazolin-5-yl | CH₂ | $C_3H_7$-iso | 4-F-phenyl | |
| 128 | 3-methyl-2-isoxazolin-5-yl | CH₃-CH | $C_3H_7$-iso | phenyl | 1.5201 |
| 129 | 3-methyl-2-isoxazolin-5-yl | CH₃-CH | $C_3H_7$-iso | 4-F-phenyl | |

Synthesis Example 5

0.8 g of 1-(2-propenyl)-4-(N-isopropyl-N-phenylcarbamoyl)-5(4H)-tetrazolinone and 1.5 g of m-chloroperoxybenzoic acid were dissolved in 50 ml of methylene chloride and the mixture was stirred for 6 hours at room temperature. After washing the reaction mixture with water, the organic layer was dried over anhydrous sodium sulfate. Then, the solvent was distilled off under reduced pressure and the residue was purified by column chromatography (chloroform) to obtain 0.5 g of 1-(2,3-epoxypropyl)-4-(N-isopropyl-N-phenylcarbamoyl)-5(4H)tetrazolinone. $n_{20}^D$: 1.5289

Synthesis Example 6

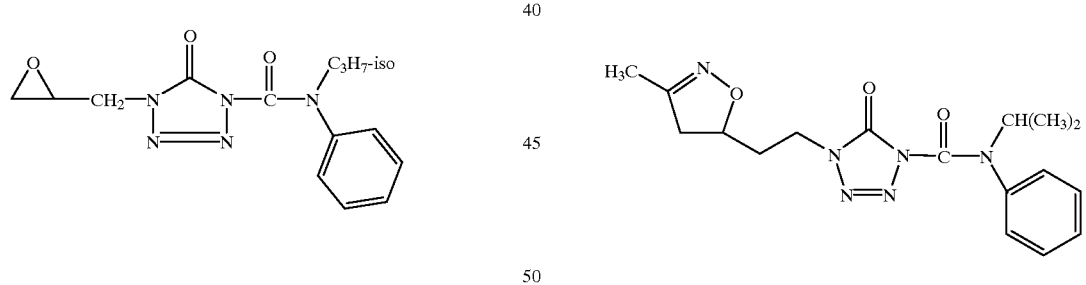

A toluene (10 ml) solution of nitroethane (0.4 g) and triethylamine (0.9 g) was added at ambient temperature to a stirring toluene (20 ml) solution of 1-(3-butenyl)-4-(N-isopropyl-N-phenylcarbamoyl)-5(4H)-tetrazolinone (1.0 g) and phenylisocyanate (0.9 g) and stirred for 18 hours. After removing the precipitate from the reaction mixture by filtration, the toluene solution was washed with water, diluted hydrochloric acid and water, dried over magnesium sulfate, and evaporated. The residue was purified by column chromatography on silica gel (n-hexane:ethyl acetate=1:1) to obtain 1-[2-(3-methyl-2-isoxazolin-5-yl)ethyl]-4-(N-isopropyl-N-phenylcarbamoyl)-5-(4H)tetrazolinone (0.7 g). m.p.: 76.5–79.5° C.

Synthesis Example 7

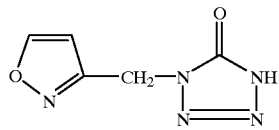

3.9 g of 3-isoxazolylmethyl isocyanate, 7.5 g of trimethylsilyl azide and a catalytic amount of boron trifluoride-ether complex were mixed and the mixture was heated under reflux for 40 hours. After allowing to cool off, excessive trimethylsilyl azide was distilled off under reduced pressure. To the residue, methanol was added. Thereafter, methanol was distilled off under reduced pressure and the residue was purified by column chromatography (ethanol/chloroform=10/100) to obtain 4.5 g of 1-(3-isoxazolylmethyl)-5(4H)-tetrazolinone. m.p.: 76–79° C.

Synthesis Example 8

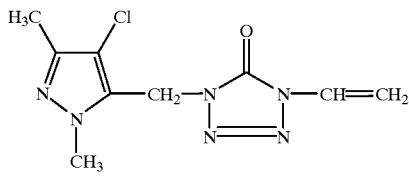

5.0 g of 4-chloro-5-chloromethyl-1,3-dimethylpyrazole, 3.0 g of 4-dimethylaminopyridine and 2.5 g of 1-ethenyl-5 (4H)-tetrazolinone were suspended in 100 ml of acetonitrile and the suspension was stirred for 5 hours at 50–55° C. After allowing to cool off the solvent was distilled off under reduced pressure. After adding 100 ml of water, the mixture was extracted with methylene chloride, and the organic layer was washed successively with water, 1Nhydrochloric acid, water and saturated saline. After drying the organic layer over anhydrous sodium sulfate, the solvent was distilled off under reduced pressure and the residue was purified by column chromatography (ethanol/chloroform=2/100) to obtain 4.2 g of 1-(4-chloro-1,3-dimethyl-5-pyrazolylmethyl)-4-ethenyl-5(4H)-tetrazolinone. m.p.: 78–79.5° C.

Synthesis Example 9

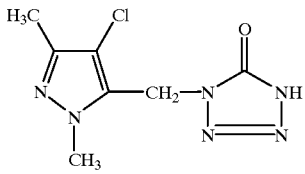

0.6 g of 1-(4-chloro-1,3-dimethyl-5-pyrazolylmethyl)-4-ethenyl-5(4H)-tetrazolinone was suspended in 30 ml of dioxane and 10 ml of water. A catalytic amount of osmium oxide [OsO$_4$] was added and the mixture was vigorously stirred for 30 minutes. Then, 1.5 g of sodium periodate was further added and the mixture was stirred for 12 hours. The reaction mixture was filtered off and the solvent was distilled off under reduced pressure until the amount of the filtrate was reduced to ¼. After adding 50 ml of water, the mixture was extracted with methylene chloride. The organic layer was dried over anhydrous sodium sulfate and then the solvent was distilled off under reduced pressure to obtain 0.4 g of 1-(4-chloro-1,3-dimethyl)-5-pyrazolylmethyl)-5 (4H)-tetrazolinone. m.p.: 157–158.5° C.

Synthesis Example 10

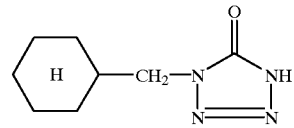

6.0 g of cyclohexylmethyl isocyanate, 10 g of trimethylsilyl azide and a catalytic amount of boron trifluoride-ether complex were mixed and the mixture was heated under reflux for 50 hours. After allowing to cool off, excessive trimethylsilyl azide was distilled off under reduced pressure. To the residue, methanol was added. Thereafter, methanol was distilled off under reduced pressure and then the residue was purified by column chromatography (chloroform=100%) to obtain 9.8 g of 1-cyclohexylmethyl-5(4H)-tetrazolinone. m.p.: 88–89° C.

Synthesis Example 11

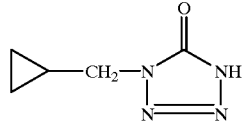

To a methanol solution of 14.2 g of cyclopropylmethylamine and 22.5 g of potassium tert-butoxide, 20 g of carbon disulfide was added dropwise under cooling with ice. After 30 minutes, 25.2 g of dimethyl sulfate was added thereto under the same condition as above and the reaction was conducted for 1 hour. After adding water to the reaction solution, the mixture was extracted with toluene and the toluene layer was washed with water. After drying the toluene solution with anhydrous magnesium sulfate, toluene was distilled off to obtain 26.3 g of methyl cyclopropylmethyldithiocarbamate. To the dithiocarbamate thus obtained, an aqueous solution of 12.7 g of sodium azide was added and reacted at 100° C. until the evolution of methylmercaptan was ceased. After allowing to cool off, the reaction solution was washed with ethyl acetate. To the aqueous layer, ethyl acetate was added, acidified with diluted hydrochloric acid and then the acidic materials were extracted with ethyl acetate. The ethyl acetate solution was washed with saturated saline, dried over anhydrous magnesium sulfate and then ethyl acetate was distilled off under reduced pressure to obtain 10 g of 1-cyclopropylmethyl-4-H-tetrazolin-5-thione. The product was dissolved in 10 ml of an aqueous solution of 3.2 g of sodium hydroxide and 6 g of propylene oxide was added thereto under cooling with ice. The reaction solution was stirred overnight. Then, the reaction solution was acidified with concentrated hydrochloric acid and extracted with chloroform. The organic layer was washed with saturated saline and dried over anhydrous magnesium sulfate. After distilling off the solvent, the residue was purified by column chromatography on silica gel (n-hexane/ethyl acetate=1:1) to obtain 5.0 g of ]-cyclopropylmethyl-5(4H)-tetrazolinone. m.p.: 61–64° C.

Synthesis Example 12

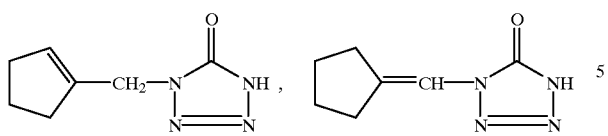

A mixture of 5.6 g of cyclopentylidene acetic acid chloride and 9.8 g of trimethylsilyl azide was heated under reflux at 100–130° C. for 48 hours. After allowing to cool off, unreacted trimethylsilyl azide was distilled off under reduced pressure. To the residue, methanol was added. Methanol was distilled off under reduced pressure and the residue was purified by column chromatography on silica gel (n-hexane/ethyl acetate=2:1–1:1) to obtain, as a by-product, 0.7 g of 1-(1-cyclopentenylmethyl)-5(4H)-tetrazolinone. The main product was 3.2, of 1-cyclopentylidenemethyl-5(4H)-tetrazolinone. m.p.: 91–93° C.

Table 2 shows the compounds of formula (II) obtained in a manner similar to those of Synthesis Examples 7 and 9–12, together with the compounds obtained in Synthesis Examples 7 and 9–12

TABLE 2

(II)

$$R^1-CH_2-(CH)_n-N\underset{N=N}{\overset{R^4}{\underset{|}{\bigg|}}}\begin{array}{c}O\\\|\\C\\\diagdown\\NH\end{array}$$

| Compound No. | $R^1$ | $(CH)_n$ with $R^4$ | m.p.(° C.) or $n_D^{20}$ |
|---|---|---|---|
| II.1 | cyclopropyl | — | 61–64 |
| II.2 | 1-cyclopentenyl | — | 91–93 |
| II.3 | cyclohexyl | — | 88–89 |
| II.4 | tetrahydrofuran-2-yl | — | 1.4989 |
| II.5 | isoxazol-3-yl | — | 76–79 |
| II.6 | 3-methylisoxazol-5-yl | — | 150–152 |
| II.7 | 3,5-dimethyl-4-methylisoxazol-4-yl | — | 124–128 |
| II.8 | 5-methylisoxazol-3-yl | — | 1.5120 |
| II.9 | 4-chloro-5-methylisoxazol-3-yl | — | — |
| II.10 | 4-chloro-3,5-dimethyl-1-methylpyrazol-4-yl | — | 157–158.5 |
| II.11 | 5-chloro-1,3,4-trimethylpyrazol-4-yl | — | 138–140.5 |
| II.12 | 4-methylfurazan-3-yl | — | 1.5073 |
| II.13 | 2,5-dimethyl-1,3,4-oxadiazol-... | — | oily |
| II.14 | 6-chloropyridin-3-yl | — | 141–142.5 |
| II.15 | pyridin-3-yl | — | — |

TABLE 2-continued (II)

$$R^1-CH_2-(CH)_n-\underset{\underset{N=N}{|}}{\overset{R^4}{N}}\underset{}{\overset{O}{\underset{}{\overset{\|}{C}}}}NH$$

| Compound No. | $R^1$ | $\underset{(CH)_n}{R^4}$ | m.p.(° C.) or $n_D^{20}$ |
|---|---|---|---|
| II.16 | (2-thienyl) | — | |
| II.17 | (thiazolyl) | — | |
| II.18 | (isothiazolyl) | — | |
| II.19 | $CH_3S$ | — | |
| II.20 | $CH_3S$ | $CH_2$ | |
| II.21 | $CH_3S(O)$ | — | |
| II.22 | $CH_3SO_2$ | — | |
| II.23 | $C_2H_5S$ | — | |
| II.24 | $n\text{-}C_3H_7S$ | — | |
| II.25 | $iso\text{-}C_3H_7S$ | — | |

Table 3 shows the compounds of formula (VIII) obtained in a manner similar to that of Synthesis Example 8, together with the compounds obtained in Synthesis Example 8.

TABLE 3

(VIII)

$$R^1-CH_2-(CH)_n-\underset{\underset{N=N}{|}}{\overset{R^4}{N}}\underset{}{\overset{O}{\underset{}{\overset{\|}{C}}}}N-CH=CH_2$$

| Compound No. | $R^1$ | $\underset{(CH)_n}{R^4}$ | m.p.(° C.) or $n_D^{20}$ |
|---|---|---|---|
| VIII.1 | 3,4,5-trimethylisoxazolyl (CH₃, CH₃) | — | 59–61.5 |
| VIII.2 | isoxazolyl | — | 1.5240 |
| VIII.3 | 4-Cl-isoxazolyl | — | oily |
| VIII.4 | 4-Cl-3,5-dimethyl-1-methylpyrazolyl (H₃C, Cl, CH₃) | — | 78–79.5 |
| III.5 | 5-Cl-1,3-dimethylpyrazolyl (H₃C—N, CH₃, Cl) | — | 96–99 |
| VIII.6 | 3,4-dimethylfurazanyl (CH₃, CH₃) | — | 76–77.5 |
| VIII.7 | 5-methyl-1,3,4-oxadiazolyl (H₃C) | — | 68–72 |

Test Example 1

Test of pre-emergence soil-treatment against plowed land weeds

Preparing method
  carrier: acetone, 5 parts by weight;
  emulsifier: benzyloxy polyglycol ether, 1 part by weight
  One part of an active compound is mixed with the above amounts of carrier and emulsifier to obtain an emulsion. A prescribed amount of this emulsion is diluted with water to prepare testing chemicals.

Testing procedure
  In the greenhouse, seeds of Echinochloa and Amaranthus lividus were sowed each in the surface layer of plowed land soil filled in a 120 cm² pot with soil-covering and a prescribed amount of the above testing chemical was uniformly spread each on the surface layer of soil in the testing pot. The herbicidal effect was examined on the day after 4 weeks from sowing. The herbicidal effect was rated as 100% in the case of complete death and as 0% in the case where equivalent growth was observed to the case of an untreated region.

Result
  The compounds of No. 1, No. 2, No. 6, No. 14, No. 30, No. 43, No. 57, No. 65 and No. 77 (as disclosed in Table 1 above) destroyed 100% of the target weeds to death by application of 1 kg/ha as the effective component.

Test Example 2

Test of post-emergence foliage treatment against plowed land weeds

Testing procedure

In the greenhouse, seeds of Echinochloa and Amaranthus lividus were sowed each in a 120 cm² pot filled with plowed land soil and covered with soil. After 10 days from sowing and soil-covering (when the weeds were at 2-foliage stage on average), each a prescribed amount of the chemical prepared similarly to those in above Test Example 1 was uniformly spread on the foliage part of tested plant in the testing pot. After 3 weeks from spreading, the extent of herbicidal effect was examined.

Result

The compounds of No. 1, No. 15, No. 57, No. 65, No. 73 and No. 85 (as disclosed in Table 1 above) destroyed 90% or more of the target weeds to death by application of 2 kg/ha as the effective component Formulation Example 1 (granules)

Twenty-five parts of water are added to a mixture of 10 parts of Compound No. 1 (see Table 1 above), 30 parts of bentonite (montmorillonite), 58 parts of talc and 2 parts of lignin sulfonate salt for well kneading followed by granulating in 10 to 40 mesh using an extrusion-granulator and drying at 40–50° C. to obtain granules.

Formulation Example 2 (granules)

A rotary mixer is charged with 95 parts of clay mineral particles having 0.2 to 2 mm of particle size distribution and 5 parts of Compound No. 14 (see Table 1 above) is sprayed therein with a liquid diluent under rotation for uniformly wetting followed by drying at 40–50° C. to give granules.

Formulation Example 3 (emulsion)

An emulsion is obtained by mixing 30 parts of Compound No. 1 (see Table 1 above), 55 parts of xylene, 8 parts of polyoxyethylene alkyl phenyl ether and 7 parts of calcium alkylbenzene sulfonate by stirring.

Formulation Example 4 (wettable powder)

A wettable powder is prepared by crushing and mixing 15 parts of Compound No. 15 (see Table 1 above), 80 parts of a mixture (1:5) of White Carbon (fine powder of hydrated amorphous silicon oxide) and powdery clay, 2 parts of sodium alkylbenzene sulphonate and 3 parts of a condensate of sodium alkylnaphthalene sulfonate and formaldehyde.

Formulation Example 5 (wettable granules)

Wettable granules are prepared by thoroughly mixing 20 parts of Compound No. 57 (see Table 1 above), 30 parts of sodium lignin sulfonate, 15 parts of bentonite and 35 parts of calcined diatomaceous earth powder, then adding water and extruding the resulting mixture through a 0.3 mm screen followed by drying.

It will be appreciated that the instant specification and the claims are set forth by way of illustration and not limitation, and that various modifications and changes may be made without departing from the spirit and scope of the present invention.

What is claimed is:

1. A tetrazolinone of the formula:

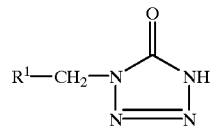

wherein

R¹ represents isoxazolyl which is optionally substituted by one or more substituents independently selected from the group consisting of $C_{1-4}$-alkyl groups.

* * * * *